United States Patent [19]

Skupin

[11] Patent Number: 5,250,286
[45] Date of Patent: Oct. 5, 1993

[54] TREATMENT OF CHRONIC OBSTRUCTIVE PULMONARY DISEASE (COPD) BY INHALATION OF AN IMIDAZOLINE

[75] Inventor: Alvaro H. Skupin, Farmington, Mich.

[73] Assignee: Aegis Technology, Inc., Wickford, R.I.

[21] Appl. No.: 799,294

[22] Filed: Nov. 27, 1991

Related U.S. Application Data

[62] Division of Ser. No. 518,716, May 7, 1990, Pat. No. 5,096,916.

[51] Int. Cl.$^5$ ............................................. A61L 9/04
[52] U.S. Cl. ................................... 424/45; 514/393; 514/398; 514/399; 514/401; 514/402; 514/826; 514/851
[58] Field of Search ............... 424/45; 514/393, 398, 514/399, 401, 402, 826, 851; 239/329, 338

[56] References Cited

U.S. PATENT DOCUMENTS 2,161,938 6/1939 Sonn .................................... 548/355
4,255,439 3/1981 Cooper ................................. 514/392

OTHER PUBLICATIONS

Kelminson et al. "The Reversibility of Pulmonars Hypotension in Patients with Cystic Fibrosis", *Pediatrics* 1967 vol. 39(1) 24–35.
Feather et al. "Effect of Tolazoline Hydrochloride on Sputum Viscosity in Cystic Fibrosis" *Thorax* (1970) No. 25 pp. 732–736.
Gross, et al., Chest, 66, 397 (1974).
Scholz, Industrial and Engineering Chemistry, 37, 120 (1945).
Gennaro, Ed., Remington's Pharmaceutical Sciences, 17th Edition, 1672–1675, 1834–1835 (1985).
Waldon, et al., Am. Rev. Respir. Dis., 130, 357 (1984).
Barnes, et al., J. of Allergy and Clinical Immunology, 68, 411 (1981).
Cotton, E. K., "Tolazoline in the Treatment of Cystic Fibrosis," The Society for Pediatric Research Program and Abstracts of the 36th Annual Meeting, p. 51 (1966).

*Primary Examiner*—Frederick E. Waddell
*Assistant Examiner*—K. Weddington
*Attorney, Agent, or Firm*—Finnegan, Henderson, Farabow, Garrett & Dunner

[57] ABSTRACT

A method of using an imidazoline compound, which is a vasodilator and an alpha-adrenergic blocking agent, for the treatment of symptoms of chronic obstructive pulmonary diseases (COPD), including cystic fibrosis, chronic bronchitis and emphysema, or COPD where it is associated with asthma, comprises administering the imidazoline to a patient by inhalation. Preferably, the imidazoline compound employed is tolazoline. The presentation of an imidazoline compound in a device for the administration of an aerosol is disclosed.

14 Claims, No Drawings

TREATMENT OF CHRONIC OBSTRUCTIVE PULMONARY DISEASE (COPD) BY INHALATION OF AN IMIDAZOLINE

This is a division of application Ser. No. 518,716, filed May 7, 1990 now U.S. Pat. No. 5,096,916.

BACKGROUND OF THE INVENTION

The present invention relates to a method for treatment of the airway obstruction found in chronic obstructive pulmonary disease (COPD), such as cystic fibrosis, chronic bronchitis, emphysema, and COPD where it is associated with asthma. This invention also relates to a device for carrying out the method.

Chronic obstructive pulmonary disease (COPD), which includes such entities as cystic fibrosis, chronic bronchitis, and emphysema, are steadily increasing in frequency, possibly due to continued smoking, increasing air pollution, and the continued aging of the population. It is estimated that in the United States alone, cystic fibrosis, a genetic disease, occurs in 1 of every 2500 births, that 8 million people have chronic bronchitis, and that 2 million individuals have emphysema. The number of deaths from these conditions, both from the complications of chronic disease and the results of acute attacks, are continuing to increase. The deaths from COPD rose from 33,000 in 1970 to 62,000 in 1983. This trend appears to be continuing.

COPD is characterized by edema of the mucous membrane, which lines the interior walls of the tracheobronchial tree. When the mucosa accumulates an abnormal quantity of liquid, the profuse and thickened serous fluid excreted may seriously affect ventilation in the alveoli. The mucus resists movement up the walls of the tracheobronchial tree, normally efficiently accomplished by the cilia throughout the airways. Consequently, the serous fluid can form mucus plugs, which can shut off alveoli or entire airways depriving whole sections of the lung of oxygen-rich air.

Plugs of mucus in the tracheobronchial tree may only partially block the flow of air through the bronchioles. This partial blockage can create a turbulent flow of air, which forms bubbles on the surface of mucosa. When there are enough bubbles, they become foam, which can clog airways and dramatically diminish respiration of the capillaries of the lungs.

The obstruction of the bronchi and bronchioles found in COPD is often a severely disabling condition. A wide variety of compounds are available with which physicians attempt to treat the symptoms of COPD. These compounds include oral methylxanthines, oral and inhaled beta-adrenergid agonists, inhaled cromolyn sodium, inhaled anticholinergics, and oral and inhaled corticosteroids. Despite the existence of these therapeutic tools, a large number of patients are not responsive to these medications or become non-responsive after a prolonged period of treatment.

The most common form of bronchoconstrictive disease is asthma, which is completely different from COPD. Pathologically, asthma involves constriction of the bronchioles, hypertrophy of the muscles of the bronchioles, and a characteristic infiltrate of eosinophils. Asthma is often treated with beta-adrenergic agonists. Some alpha-adrenergic receptor antagonists have been studied in man to examine their possible therapeutic utility in asthma. Barnes et al. (*J. All. and Clin. Immun.*, 68:411–415, 1981) studied prazosin by inhalation in 10 asthmatic patients and showed that it reduced post-exercise bronchoconstriction. Gross et al. (Chest, 66:397–401, 1974) studied one asthmatic patient and found that phentolamine blocked exercise-induced bronchoconstriction when administered orally or by inhalation. On the other hand, Walden et al. (*Am. Rev. Respir. Dis.*, 130:357–362, 1984) found in 8 asthmatics that oral phentolamine relieved bronchoconstriction in exercise-induced asthma, but not in asthma induced by ragweed. Despite these encouraging results, alphaadrenergic receptor antagonists are not currently available for the treatment of asthma by the inhalation route.

In distinction to asthma, cystic fibrosis, chronic bronchitis, and emphysema are typically treated with agents to dry up the secretions and with antibiotics to combat infection. The beta-adrenergic agonists, which work so well in the treatment of asthma, are typically ineffective for treatment of COPD. This may be a predictable result in that as the mechanisms of the diseases differ dramatically, one would not expect a successful treatment of a constriction of the bronchi and bronchioles to be applicable to a blockage of the bronchi and bronchioles. At the present time, no alpha-adrenergic receptor antagonist is available for use by the inhalation route for the treatment of any form of COPD.

There exists a need in the art for an effective treatment for chronic obstructive pulmonary diseases, such as cystic fibrosis, chronic bronchitis, and emphysema, and COPD where it is associated with asthma. The treatment should involve the use of a pharmaceutical composition that is easy to administer to a patient in need of therapy. Ideally, it should be possible for the treatment to be self-administered. In addition, there exists a need in the art for a device for the treatment of COPD.

SUMMARY OF THE INVENTION

This invention aids in fulfilling these needs in the art. In accordance with the present invention, imidazoline compounds are employed for the treatment of the symptoms of airway obstruction of various forms of chronic obstructuve pulmonary disease. More particularly, the present invention provides a method for the treatment of COPD, which comprises administering to a patient an alpha-adrenergic blocking agent of the formula

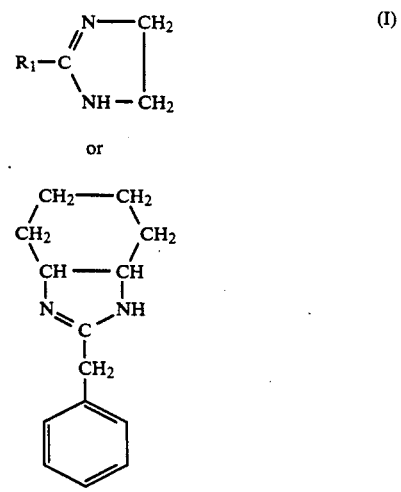

wherein $R_1$ is at least one alkyl group, an alkoxy group, an unsubstituted phenyl group, a phenyl group containing 1 or 2 substituents independently selected from the group consisting of unsubstituted alkyl and unsubstituted alkoxy groups, or

where $R_2$ is a branched or straight chain $C_1$ to $C_5$ alkylene group or a branched or straight chain $C_1$ to $C_5$ alkenylene group, n is 1 or 2, and each X is independently selected from the group consisting of hydrogen, unsubstituted alkyl, and unsubstituted alkoxy groups. The alpha-adrenergic blocking agent is also a vasodilator and is administered by the novel route of inhalation. In a preferred embodiment of the present invention, tolazoline, which is chemically designated as 2-benzyl-4,5-imidazoline hydrochloride, is employed as the alpha-adrenergic blocking agent.

This invention also provides an apparatus comprising a device having a container for an alpha-adrenergic blocking agent of the above formula. The apparatus includes means in communication with the container for delivering a predetermined amount of the blocking agent such that the respiratory distress of COPD is alleviated when the predetermined amount is administered to a patient by the inhalation route.

As previously described, it was found that asthma may be treated with beta-adrenergic agonists and it was suggested that alpha-adrenergic antagonists may be useful in some types of asthma. In contrast, the beta-adrenergic agonists were found to be typically ineffective in cases of cystic fibrosis, bronchitis, and emphysema. Consequently, the discovery that an alpha-adrenergic antagonist, such as tolazoline, as an effective treatment for COPD was wholly unexpected.

DESCRIPTION OF PREFERRED EMBODIMENTS

This invention is useful for the treatment of a subject having chronic obstructive pulmonary disease, including cystic fibrosis, chronic bronchitis, emphysema, and COPD where it is associated with asthma. The physiological effects of these diseases are extremely varied, but subjects treated according to this invention have airway resistance that increases the work of breathing. The subject exhibits difficulty in moving air from the lungs or through the bronchioles during expiration. This invention makes it possible to ameliorate the effects of these diseases by improving lung function as evidenced by an increase in the amount of air the subject can forcibly exhale in a single breath. It will be understood that the invention also relates to the treatment of subjects with COPD to relieve other physiological effects of the disease or pathophysiological events associated with the disease. Thus, it will be understood that the invention encompasses the treatment of a subject, for example, to restore capillary function diminished by COPD or to provide oxygen to sections of the lung deprived by COPD.

This invention is carried out with an imidazoline of the following formula:

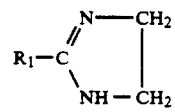

or

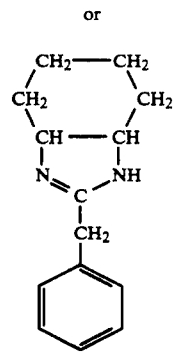

wherein $R_1$ is at least one alkyl group, an alkoxy group, an unsubstituted phenyl group, a phenyl group containing 1 or 2 substituents independently selected from the group consisting of unsubstituted alkyl and unsubstituted alkoxy groups, or

where $R_2$ is a branched or straight chain $C_1$ to $C_5$ alkylene group or a branched or straight chain $C_1$ to $C_5$ alkenylene group, n is 1 or 2, and each X is independently selected from the group consisting of hydrogen, unsubstituted alkyl, and unsubstituted alkoxy groups.

The imidazoline employed in this invention is a vasodilator agent. That is, when a non-toxic dose of the imidazoline of formula (I) is administered to a mammal, such as a human, by intravenous injection there is a lowering of systemic blood pressure by at least about 10 to 100 mm of mercury in the mammal. Imidazolines that are vasoconstrictors have not been found to be effective in the treatment of COPD.

When the substituent $R_1$ in the imidazoline of formula (I) is an alkyl or an alkoxy radical, the chain length of the alkyl and alkoxy radicals is not limited to a specific length, but is preferably less than about 10 carbons, and especially about 1 to about 4 carbon atoms. The alkyl and alkoxy groups are generally straight chain.

When the substituent $R_1$ in the imidazoline of formula (I) is a phenylmethyl group, the imidazoline is the known compound tolazoline. Tolazoline is the preferred compound for use in the present invention. The structural formula of tolazoline is as follows:

The empirical formula is $C_{10}H_{12}N_2HCl$. Tolazoline has a molecular weight of 196.69, is freely soluble in water and alcohol, and exhibits vasodilator effects. Tolazoline is very slightly soluble in ether or ethyl acetate. Aqueous solutions are slightly acid. A 2.5% solution of tolazoline in water has a pH of about 4.9 to about 5.3. Crystals of tolazoline have a melting point of about 174° C.

When the substituent $R_1$ in the imidazoline of formula (I) is a substituted phenylmethyl group, the phenyl moiety can be substituted by 1, 2, or 3 alkoxy or alkyl radicals containing less than about 10, and preferably about 1 to about 4 carbon atoms. The substitution of the phenylmethyl radical is preferably limited at the para position. Preferably, the imidazoline compound is substituted at the 2-position of the imidazoline ring.

Vasodilators employed in the invention are preferably alkylated imidazolines or 2-arylkylated imidazolines. The preferred 2-arylkylated imidazolines employed in the invention are substituted or unsubstituted 2-benzylimidazolines. Alkylated imidazolines, which have a vasoconstrictive effect, comprise, for example, certain alkyl derivatives, 2-cyclohexylmethyl imidazoline, and 2-cyclohexenylmethyl imidazoline.

2-Benzylimidazolines can be substituted on the imidazoline ring, on the methylene group which forms the carbon atom bridge between the imidazoline ring and the benzene ring, or on the benzene ring. Vasodilators with substituents on the imidazoline ring are preferably substituted on the 4- or 5-carbon atoms. Substitutions on the nitrogen atom may reverse action on the circulatory system and result in compounds that act as vasoconstrictors, rather than vasodilators.

2-Benzylimidazolines can also be substituted on the methylene group without changing the vasodilator effect of the compound. Substituents on the methylene group can be in the form of a side chain or result in a lengthening of the carbon bridge between the imidazoline ring and the benzene moiety.

Finally, 2-benzylimidazoline can be substituted, for example, on the benzene ring with methyl or methoxy groups. A para-methyl substituent, a methylation of a pra-hydroxy substituent, or a methylation of a dihydroxy substituent can produce an imidazoline with vasodilator activity.

A preferred group of compounds that can be employed in this invention are alpha-adrenergic blocking agents of the formula:

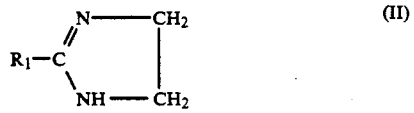

(II)

wherein $R_1$ is a $C_1$-$C_4$ alkyl group, a $C_1$-$C_4$ alkoxy group, an unsubstituted phenylmethyl group, a phenylmethyl group containing 1 or 2 substituents independently selected from the group consisting of unsubstituted $C_1$-$C_4$ alkyl groups and unsubstituted $C_1$-$C_4$ alkoxy groups.

Specific examples of imidazolines with vasodilator effect that can be employed in this invention include, but are not limited to:
  2-alkylimidazolines;
  2-phenylimidazoline;
  2-benzylimidazoline;

alkylbenzylimidazolines, such as dimethylbenzylimidazoline, ethylbenzylimidazoline, and propylbenzylimidazoline; and alkoxybenzyl imidazolines, such as ethoxybenzylimidazoline, propyloxybenzylimidazoline, butyloxybenzylimidazoline.

Substitution of the aromatic ring with functional groups, such as hydroxy, methoxy, and others, but particularly a hydroxyl substitution, can form a vasoconstrictor. Substituents on the methylene bridge with functional groups, such as hydroxy and methoxy, can also generally form vasoconstrictors. Finally, compounds containing naphthyl radicals are generally powerful vasoconstrictors.

The imidazoline of formula (I) can be obtained by reacting an iminoether of the formula:

(II)

wherein:
  R is defined as in compound (I); and
  $R_2$ is an alkyl radical having 1 to about 10 carbon atoms; with an ethylene diamine.

The iminoether of formula (II) can be in the form of a free base or a salt of a mineral acid. The reaction of the iminoether with ethylene diamine can be carried out in the presence or absence of a solvent. When a solvent is employed, an alkanol or an alkyl polyhalide is suitable. Examples of specific solvents are methanol, ethanol, butanol, and 1,3-dichloropropane.

The iminoether employed as a starting material can be produced from a corresponding nitrile by dissolving the nitrile in an alkanol. The resulting nitrile-alkanol solution can be mixed at a low temperature with a mineral acid and allowed to stand for several hours. The solvent can then be removed under reduced pressure at as low a temperature as possible to produce the salt of the iminoether.

The reaction of the iminoether with ethylene diamine can be carried out in a reaction medium at room temperature or at an elevated temperature. When the reaction is conducted at a low temperature employing a free iminoether, a gas is preferably passed through the reaction medium to remove ammonia formed as a by-product of the reaction. Examples of suitable gases are nitrogen, fluorine, or beryllium gas.

When the reaction of the iminoether with ethylene diamine is conducted in the absence of a solvent employing a free iminoether, crude imidazoline can be obtained at the completion of the reaction. Cessation of the evolution of ammonia characterizes completion of the reaction.

The crude imidazoline can be purified by distillation or crystallization. When the reaction is conducted in the presence of a solvent employing a salt of an iminoether, the solvent can be distilled when the evolution of ammonia is completed. The resulting residue can then be recrystallized or mixed with a strong base and extracted with an organic solvent insoluble in water. The extraction solution can be dried with an alkaline drying agent, the solvent expelled, and residual imidazoline base can be either distilled or recrystallized. The synthesis of imidazoline compounds is delineated in U.S. Pat. No. 2,161,938.

The imidazoline compound of formula (I) can be employed in this invention in the form of a free base or a water soluble, pharmaceutically acceptable salt. The use of a salt is preferred when the imidazoline is administered in solution to the patient because imidazoline salts are generally more soluble in aqueous solvents. Examples of suitable salts are the salts of strong mineral acids, such as hydrochloric acid, sulfuric acid, or phosphoric acid. A preferred imidazoline compound for use in the invention is a tolazoline hydrochloride salt. The imidazoline compound can also be employed in free or uncombined form, such as when administered in the form of a powder or emulsion to the patient.

The imidazolines employed in the present invention can also be admixed with solid or liquid pharmaceutically acceptable nontoxic carriers, diluents and adjuvants, including appropriate surfactants, in order to prepare the composition for use and to aid in administration to the patient by inhalation. Such pharmaceutical carriers can be sterile liquids, such as water and oils, including those of petroleum, animal, vegetable or synthetic origin. Water is a preferred carrier. Saline solutions can also be employed as liquid carriers. For example, about 25 to about 100 mg of the imidazoline can be dissolved in saline solution at a concentration up to about 40 mg/ml to form a pharmaceutical composition suitable for administration by the inhalation route. Surfactants such as polyoxyethylene fatty acid esters polyoxyethylene sorbitan acid esters, or glyceryl esters, for example, may be employed. Other suitable pharmaceutical carriers are described in *Remington's Pharmaceutical Sciences* by E. W. Martin. A pH in the range of about 4.5 to 5.5 is preferred. The pH can be adjusted with a conventional pharmaceutically acceptable buffer.

The imidazoline of formula (I) can be administered to the patient by means of a pharmaceutical delivery system for the inhalation route. The pharmaceutical delivery system is one that is suitable for respiratory therapy by topical administration of the imidazoline to mucosal linings of the tracheobronchial tree. For example, this invention can utilize a system that depends on the power of a compressed gas to expel the imidazoline from a container. See Sciarra et al, *Theory and Practice of Industrial Pharmacy*, 1976:270–295, which is relied upon and incorporated by reference herein. An aerosol or pressurized package can be employed for this purpose.

As used herein, the term "aerosol" is used in its conventional sense as referring to very fine liquid or solid particles carried by a propellant gas under pressure to a site of therapeutic application. When a pharmaceutical aerosol is employed in this invention, the aerosol contains the therapeutically active imidazoline, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient.

The propellant of an aerosol package containing the imidazoline should be capable of developing pressure within the container to expel the imidazoline when a valve on the aerosol package is opened. Various types of propellants can be utilized. Fluorinated hydrocarbons, such as trichloromonofluromethane (propellant 11), dichlorodifluoromethane (propellant 12), and dichlorotetrafluoroethane (propellant 114), as well as compressed gases such as nitrogen, carbon dioxide, nitrous oxide, or Freon, can be employed as propellants for a pharmaceutical aerosol. The vapor pressure of the aerosol package is determined by the propellant or propellants that are employed. By varying the proportion of each component propellant, any desired vapor pressure can be obtained within the limits of the vapor pressure of the individual propellants.

The present invention can also be carried out with a nebulizer, which is an instrument that generates very fine liquid particles of substantially uniform size in a gas. Preferably, a liquid containing the imidazoline is dispersed as droplets about 5 mm or less in diameter in the form of a mist. The small droplets can be carried by a current of air or oxygen through an outlet tube of the nebulizer. The resulting mist penetrates into the respiratory tract of the patient.

A powder composition containing an imidazoline of formula (I), with or without a lubricant, carrier, or propellant, can be administered to a patient in need of therapy. This embodiment of the invention can be carried out with a conventional device for administering a powder pharmaceutical composition by inhalation.

The patient to be treated can be a primate, such as a human, or any other animal exhibiting characteristic symptoms of COPD. While the method of the invention is especially adapted for the treatment of a human patient, it will be understood that the invention is also applicable to veterinary practice.

The imidazoline of formula (I) is administered to the patient by inhalation in an amount sufficient to alleviate the respiratory distress of chronic obstructive pulmonary disease. The dosages and necessity of subsequent dosages are dependent upon the severity of the respiratory distress. The dosages are also dependent upon the individual characteristics of each patient. An animal may require smaller or larger dosages dependent upon the weight or airway structure of the subject. A patient's age, sex, race, or other distinguishing characteristics can also be determinative.

A prototypical treatment schedule for a patient suffering from respiratory distress comprises: 1) An initial dose of about 4 to 12 mg of an imidazoline compound, and 2) subsequent dosages of about 5 to 100 mg of an imidazoline compound, as necessary.

The necessity for repeated doses can be determined by observing the amount of airway obstruction present after the initial dose. It will be understood that these dosages are the amounts of the imidazoline compound that actually get to the patient. Thus, for example, when a commercially available saline solution containing about 25 mg of tolazoline (Ciba-Geigy) is administered by means of a nebulizer to a patient, of the approximately 25 mg of the imidazoline compound available in the nebulizer, about 4 to 12 mg is actually delivered to the patient. Typically, the patient receives one dose from the nebulizer, which contains approximately 25 mg of an imidazoline compound, delivering approximately 4 to 12 mg of the compound to the patient, every 3 to 5 minutes until a response occurs. Subsequently, dosages can be given every 4 to 8 hours, as necessary.

Relief of the airway obstruction can be typically demonstrated by measuring an increase in Forced Expiratory Volume in One Second ($FEV_1$), and other standard measurements. This invention makes it possible to achieve about 15 to about 48 percent increase in FEV1 measurements within about 10 to about 30 minutes after administration of the imidazoline to the patient by inhalation. $FEV_1$ can be determined by conventional techniques. See A. Fishman, TEXTBOOK OF PULMONARY DISEASES (1989).

The apparatus of this invention comprises a container, an amount of a vasodilator of formula (I) in the container, and means in communication with the container for delivering a dosage of the imidazoline to the patient. The dosage is that amount that is at least sufficient to alleviate the respiratory distress associated with COPD when the dosage is administered to the patient by the inhalation route. The dosage should be reproducible not only for each dose delivered from the same package, but also from package to package. The dosage of the imidazoline can be regulated, for example, by a metering valve capable of accurately delivering a measured amount of the imidazoline. Generally, valves for upright use are employed with solution type aerosols, while inverted valves are employed with suspension or dispersion aerosols.

Various materials can be employed as containers for aerosols and nebulizers. Glass, stainless steel, aluminum, and chemically resistant containers are preferred as these materials possess excellent compatibility with drugs.

Having generally described the invention, a more complete understanding can be obtained by reference to specific examples, which are provided herein for purposes of illustration only and are not intended to be limiting.

EXAMPLE 1

The effects of tolazoline were demonstrated in a 26 year old white female patient with a past history of cystic fibrosis, a condition known to have as one of its complications COPD. The patient was using at home a combination therapy of an inhaled beta-adrenergic receptor agonist and an inhaled steroid. Despite this therapy, the patient presented in the emergency room was in respiratory distress. Objective pulmonary function tests confirmed the greatly reduced pulmonary function in this patient and demonstrated that the beta-adrenergic agonist was not effective.

Tolazoline therapy resulted in great improvement in the subjective sense of well being of the patient and great improvement in the objective pulmonary function tests.

The patient was discharged from the emergency room and returned home. The results of the pulmonary function tests are presented in Table 1.

TABLE 1

PULMONARY FUNCTION OF CYSTIC FIBROSIS PATIENT

| TEST | Pretreatment Values | | |
|---|---|---|---|
| | Actual value | Normal value | Percent of normal |
| FVC (liters) | 1.31 | 3.36 | 39% |
| $FEV_1$ (liters) | 0.65 | 2.91 | 22% |
| PEFR (liters/sec) | 1.4 | 6.35 | 22% |
| | 10 Minutes After Tolazoline | | |
| TEST | Pretreat value | Post-treat value | Percent change |
| FVC (liters) | 1.31 | 1.42 | +3% |
| $FEV_1$ (liters) | 0.65 | 0.64 | 0% |
| PEFR (liters/sec) | 1.4 | 1.4 | 0% |
| | 20 Minutes After Tolazoline | | |
| | Pretreat | Post-treat | Percent |

TABLE 1-continued

PULMONARY FUNCTION OF CYSTIC FIBROSIS PATIENT

| TEST | value | value | change |
|---|---|---|---|
| FVC (liters) | 1.31 | 2.49 | +90.1% |
| $FEV_1$ (liters) | 0.65 | 0.87 | +33.8% |
| PEFR (liters/sec) | 1.4 | 1.7 | +21.7% |

Abbreviations:
FVC-Forced Vital Capacity
$FEV_1$-Forced Expiratory Volume in One Second
PEFR-Peak Expiratory Flow Rate.

EXAMPLE 2

A 28 year old white female with a history of cystic fibrosis was hospitalized because of an acute exacerbation of chronic bronchitis. Pulmonary function tests confirmed reduced pulmonary function.

The patient was first treated with a beta-adrenergic receptor agonist (Albuterol), which was ineffective. Tolazoline was then administered as described above. Improvement was shown in the pulmonary function test. Results are presented in Table 2.

TABLE 2

PULMONARY FUNCTION OF CYSTIC FIBROSIS PATIENT WITH CHRONIC BRONCHITIS

| TEST | Pretreatment Values | | |
|---|---|---|---|
| | Actual Value | Normal Value | Percent of normal |
| FVC (liters) | 2.55 | 3.45 | 74% |
| $FEV_1$ (liters) | 1.59 | 2.98 | 54% |
| PEFR (liters/sec) | 3.54 | 6.41 | 55% |
| | Albuterol Treatment Values | | |
| TEST | Pretreat Value | Post-treat Value | Percent Change |
| FVC (liters) | 2.55 | 2.52 | −1% |
| $FEV_1$ (liters) | 1.59 | 1.58 | −1% |
| PEFR (liters/sec) | 3.54 | 2.94 | −17% |
| | Tolazoline Treatment Values | | |
| TEST | Pretreat Value | Post-treat Value | Percent Change |
| FVC (liters) | 2.41 | 2.72 | 13% |
| $FEV_1$ (liters) | 1.54 | 1.79 | 16% |
| PEFR (liters/sec) | 3.02 | 4.16 | 38% |

EXAMPLE 3

A 29 year old black male with a history of asthma was presented in respiratory distress. Pulmonary function tests confirmed greatly reduced pulmonary function. Tolazoline was administered as described above. Great improvement resulted as evidenced by the pulmonary function test at both 10 and 20 minutes post-tolazoline treatment. Results are presented in Table 3.

TABLE 3

PULMONARY FUNCTION OF PATIENT WITH RESPIRATORY DISTRESS ACCOMPANYING ASTHMA

| TEST | Pretreatment Values | | |
|---|---|---|---|
| | Actual Value | Normal Value | Percent of normal |
| FVC (liters) | 1.68 | 5.12 | 32.8% |
| $FEV_1$ (liters) | 0.99 | 4.33 | 22.9% |
| PEFR (liters/sec) | 1.59 | 8.26 | 19.2% |
| | 10 Minutes After Tolazoline | | |
| TEST | Pretreat Value | Post-treat Value | Percent Change |
| FVC (liters) | 1.68 | 2.96 | 76% |

TABLE 3-continued

| PULMONARY FUNCTION OF PATIENT WITH RESPIRATORY DISTRESS ACCOMPANYING ASTHMA | | | |
|---|---|---|---|
| $FEV_1$ (liters) | 0.99 | 1.20 | 21.2% |
| PEFR (liters/sec) | 1.59 | 1.64 | 3% |

| | 20 Minutes After Tolazoline | | |
|---|---|---|---|
| TEST | Pretreat Value | Post-treat Value | Percent Change |
| FVC (liters) | 1.68 | 3.18 | 89% |
| $FEV_1$ (liters) | 0.99 | 1.47 | 48.4% |
| PEFR (liters/sec) | 1.59 | 1.75 | 10% |

In all cases, therapy consisted of approximately 25 mg of tolazoline administered in a saline aerosol by means of an air driven nebulizer. Approximately 4 to 12 mg of tolazoline is delivered to the patient. A saline solution containing the tolazoline is commercially available as Priscoline ®, distributed by Ciba-Geigy Corporation. The nebulizer, Pulmo-Aide ®, was obtained from DeVilbiss Healthcare Worldwide.

The objective data in these patients demonstrates that tolazoline when administered by the inhalation route was able to markedly improve the pulmonary function of these patients. The improvement in Vital Capacity, up to 90%, the increase in Forced Expiratory Volume, up to 48%, and the increase in Peak Expiratory Flow Rate, up to 21%, were dramatic changes for the better.

In summary, this invention provides a new, effective therapy for the treatment of symptoms of the airway obstruction found in COPD. This therapy utilizes a drug with a relatively low probability for producing serious side effects; the drug can be administered to a patient in a manner that minimizes the number of systemic side effects. The imidazoline compounds can be administered in an aerosol form, which is inhaled in order to treat the symptoms of the airway obstruction found in COPD. The apparatus of the invention can be a hand held or portable device, which can produce an aerosol for inhalation. These and other results have been attained by providing a method of relieving the airway obstruction found in COPD by the administration, by the inhalation route to a patient afflicted with such airway obstruction, an amount of an imidazoline compound sufficient to reduce the airway obstruction as demonstrated by objective measurements.

Having now fully described the invention, it will be apparent to one of ordinary skill in the art that many changes and modifications can be made thereto without departing from the spirit or scope of the invention as set forth herein. It is intended that the invention be limited solely by the lawful scope of the appended claims.

What is claimed is:

1. An apparatus for administering a pharmaceutical composition to a patient by inhalation, wherein the apparatus comprises:

a container containing an alpha-adrenergic blocking agent of the formula

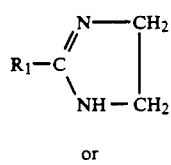

or

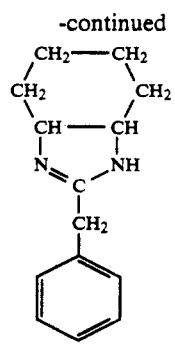

wherein
$R_1$ is at least one alkyl group, an alkoxy group, an unsubstituted phenyl group, a phenyl group containing 1 or 2 substituents independently selected from the group consisting of unsubstituted alkyl and unsubstituted alkoxy groups, or where $R_2$ is a branched or straight chain $C_1$ to $C_5$ alkylene group or a branched or straight chain $C_1$ to $C_5$ alkenylene group,
n is 1 or 2, and
each X is independently selected from the group consisting of hydrogen, unsubstituted alkyl, and unsubstituted alkoxy groups; and
means in communication with the container for delivering to a patient a dosage of the alpha-adrenergic blocking agent at least sufficient to alleviate the respiratory distress of chronic obstructive pulmonary disease or COPD where it is associated with asthma.

2. The apparatus of claim 1, wherein the alpha-adrenergic blocking agent is substituted in the 2-position of the imidazoline ring.

3. The apparatus of claim 1, wherein the alpha-adrenergic blocking agent is tolazoline.

4. The apparatus of claim 1, wherein the dosage amount is about 4 to about 100 mg.

5. The apparatus of claim 3, wherein the dosage delivered to the patient is about 4 to 12 mg.

6. The apparatus of claim 4, wherein the imidazoline compound is admixed with a pharmaceutically acceptable carrier.

7. The apparatus of claim 1, wherein said apparatus comprises means for providing said dosage in aerosol form.

8. The apparatus of claim 1, wherein said apparatus is a nebulizer.

9. The apparatus of claim 1, wherein said dosage is an inhalable powder.

10. An apparatus for administering a pharmaceutical composition to a patient for inhalation, wherein the apparatus comprises:

a container containing an alpha-adrenergic blocking agent of the formula

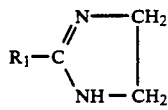

or

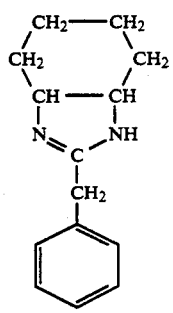

wherein

R¹ is at least one alkyl group, an alkoxy group, an unsubstituted phenyl group, a phenyl group containing 1 to 2 substituents independently selected from the group consisting of unsubstituted alkyl and unsubstituted alkoxy groups, or

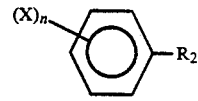

where $R_2$ is a branched or straight chain $C_1$ to $C_5$ alkylene group or a branched or straight chain $C_1$ to $C_5$ alkenylene group, n is 1 or 2, and each X is independently selected from the group consisting of hydrogen, unsubstituted alkyl, and unsubstituted alkoxy groups; and means in communication with the container for delivering to a patient a dosage of about 4 to about 100 mg of the alphaadrenergic blocking agent at least sufficient to alleviate the respiratory distress of chronic obstructive pulmonary disease or COPD where it is associated with asthma.

11. The apparatus of claim 10, wherein the alphaadrenergic blocking agent is tolazoline.

12. The apparatus of claim 11, wherein said apparatus comprises means for providing said dosage in aerosol form.

13. The apparatus of claim 12, wherein the dosage delivered to the patient is about 4 to 12 mg.

14. The apparatus of claim 13, wherein the tolazoline is admixed with a pharmaceutically acceptable carrier.

* * * * *